United States Patent [19]

Murphy et al.

[11] Patent Number: 5,516,657
[45] Date of Patent: May 14, 1996

[54] BACULOVIRUS VECTORS FOR EXPRESSION OF SECRETORY AND MEMBRANE-BOUND PROTEINS

[75] Inventors: Cheryl I. Murphy, Hopkinton; Elihu Young, Sharon, both of Mass.

[73] Assignee: Cambridge Biotech Corporation, Worcester, Mass.

[21] Appl. No.: 29,402

[22] Filed: Mar. 5, 1993

Related U.S. Application Data

[63] Continuation-in-part of Ser. No. 880,647, May 11, 1992, abandoned.

[51] Int. Cl.$^6$ .......................... C12N 15/86; C12N 15/63
[52] U.S. Cl. ................. 435/69.3; 435/69.1; 435/69.8; 435/172.1; 435/172.3; 435/320.1
[58] Field of Search .............................. 435/320.1, 69.1, 435/69.8, 69.3, 172.1, 172.3; 536/23.1, 24.1

[56] References Cited

U.S. PATENT DOCUMENTS 5,278,050  1/1994  Summers ............................... 435/69.1

OTHER PUBLICATIONS

Pharmingen 1992–1993 Catalog Supplement, pp. 12–13 (1993).
Stewart, L. M. D. et al., "Construction of an improved baculovirus insecticide containing an insect–specific toxin gene," *Nature* 352:85–88 (4 Jul. 1991).
Cheryl L. I. Murphy, et al., "The Role of Glycosylation in the Interaction of Recombinant CD4 and HIV Envelope Proteins from Baculovirus Infected Insect Cells," Abstract No. L 436, HIV and AIDS: Pathogenesis, Therapy and Vaccine, held Mar. 31–Apr. 6, 1990.
Murphy, C. I. et al., "Temporal Expression of HIV–1 Envelope Proteins in Baculovirus-Infected Insect Cells: Implications for Glycosylation and CD4 Binding," *GATA* 7(6):160–171 (1990).
Jarvis, D. L. et al., "Glycosylation and Secretion of Human Tissue Plasminogen Activator in Recombinant Baculovirus-–Infected Insect Cells," *Mol. and Cell. Biol.* 9(1):214–223 (1989).
Bailey, M. J. et al., "Glycosylation Is Not Required for the Fusion Activity of the G Protein of Vesicular Stomatitis Virus in Insect Cells," *Virology* 169:323–331 (1989).
O'Reilly, D. R. et al., "A Baculovirus Blocks Insect Molting by Producing Ecdysteroid UDP–Glucosyl Transferase," *Science* 245:1110–1112 (1989).
O'Reilly, D. R. et al., "Regulation of Expression of a Baculovirus Ecdysteroid UDP glucosyltrans–ferase Gene," *J. Virol.* 64(3):1321–1328 (1990).

Whitford, M. et al., "Identification and Sequence analysis of a Gene Encoding gp67, an Abundant Envelope Glycoprotein of the Baculovirus Autographa californica Nuclear Polyhedrosis Virus," *J. Virol.* 63(3): 1393–1399 (1989).
Vaughn, J. L. et al., "The Establishment of Two Cell Lines From the Insect Spodoptera Frugiperda (Lepidoptera: Noctuidae)," *In Vitro* 13(4):213–217 (1977).
Tessier, D. C. et al., "Enhanced secretion from insect cells of a foreign protein fused to the honeybee melittin signal peptide," *Gene* 98:177–183 (1991).
Devlin, J. J. et al., "Novel Expressin of Chimeric Plasminogen Activators in Insect Cells," *Biotechnol.* 7:286–292 (1989).
Summers, M. D. et al., "A Manual of Methods for Baculovirus Vectors and Insect Cell Culture Procedures," In: *Texas Agricultural Experiment Station Bulletin No. 1555*, May, 1987.
Broussard, D. R. et al., "Effects of Serum Concentration and Media Composition on the Level of Polyhedrin and Foreign Gene Expressin by Baculovirus Vectors," *J. Invert. Path.* 54:144–150 (1989).
Culp, J. S. et al., "Regulated Expression Allows High Level Production and Secretion of HIV–1 gp120 Envelope Glycoprotein in Drosophila Schneider Cells," *Biotechnol.* 9:173–177 (1991).
Jarvis, D. L. et al., "Use of Early Baculovirus Promoters for Continuous Expression and Efficient Processing of Foreign Gene Products in Stably Transformed Lepidopteran Cells," *Biotechnol.* 8: 950–955 (1990).
Ratner, L. et al., "Complete nucleotide sequence of the AIDS virus, HTLV–III," *Nature* 313:277–284 (1985).
Luckow, V. A. et al., "High Level Expression of Nonfused Foreign Genes with Autographa californica Nuclear Polyhedrosis Virus Expression Vectors," *Virol.* 170:31–39 (1989).
Matsuura, Y. et al., "Baculovirus Expression Vectors: the Requirements for High Level Expression of Proteins, Including Glycoproteins," *J. Gen. Virol.* 68:1233–1250 (1987).

*Primary Examiner*—Mindy B. Fleisher
*Assistant Examiner*—David Guzo
*Attorney, Agent, or Firm*—Sterne, Kessler, Goldstein & Fox

[57] ABSTRACT

The invention provides *Baculovirus* vectors comprised of a promoter upstream from a signal peptide. The *Baculovirus* vectors allow for the expression of a glycosylated protein in the late term of *Baculovirus* infection. Methods for the construction of such a *Baculovirus* vector are also provided. In addition, methods for producing large amounts of a desired glycosylated protein in the late term infection of *Baculovirus* infection are also provided.

18 Claims, 10 Drawing Sheets

GATCT AAT ATG ACT ATC CTT TGC TGG CTG GCC CTT CTG TCA ACT CTG ACT GCC GTC AAC GCT GCC
A TTA TAC TGA TAG GAA ACC GAC CGG GAA CGG CAG TGA GAC AGT TGA GAC TGA CGG CAG TTG CGA CGC CAT G
      M   T   I   L   C   W   L   A   L   L   S   T   L   T   A   V   N   A   A

α   α   α   α   α   α   α   α   α   α   α   α   α   α   α   α   α   α   α   α   α   α   α   α

EGT SIGNAL PEPTIDE

FIG.1

```
         10        20        30        40        50        60        70        80        90       100
          *         *         *         *         *         *         *         *         *         *
GATC ATG GTA AGC GCT ATT GTT TTA TAT GTG CTT TTG GCG GCG GCG CAT TCT GCC TTT GCG GCG GCG GAG CAC TGC AAC G GATCC TAAGT AGGTA G
TAC CAT TCG CGA TAA CAA AAT ATA CAC GAA AAC CGC CGC GCG GTA AGA CGG AAA CGC CGC CGC CTC GTG ACG TTG C CTAGG ATTCA TCCAT CCATG
  M   V   S   A   I   V   L   Y   V   L   L   A   A   A   H   S   A   F   A   A   A   E   H   C   N>
                                          pP67 SIGNAL PEPTIDE 10        20        30        40        50        60        70        80        90       100
          *         *         *         *         *         *         *         *         *         *
GATC ATG GTA AGC GCT ATT GTT TTA TAT GTG CTT TTG GCG GCG GCG CAT TCT GCC TTT GCG GCG GCG GAG CAC TGC AAC G GGATC CTAAG TAGGT AG
TAC CAT TCG CGA TAA CAA AAT ATA CAC GAA AAC CGC CGC CGC CCC GTA AGA CGG AAA CGC CGC CGC CTC GTG ACG TTG C CCTAG GATTC ATCCA TCCAT G
  M   V   S   A   I   V   L   Y   V   L   L   A   A   A   H   S   A   F   A   A   A   E   H   C   N>
                                          pP67 SIGNAL PEPTIDE 10        20        30        40        50        60        70        80        90       100
          *         *         *         *         *         *         *         *         *         *
GATC ATG GTA AGC GCT ATT GTT TTA TAT GTG CTT TTG GCG GCG GCG CAT TCT GCC TTT GCG GCG GCG GAG CAC TGC AAC GG GGAT CCTAA GTAGG TAG
TAC CAT TCG CGA TAA CAA AAT ATA CAC GAA AAC CGC CGC CGC CCC GTA AGA CGG AAA CGC CGC CGC CTC GTG ACG TTG CC CCTA GGATT CATCC ATCCA TG
  M   V   S   A   I   V   L   Y   V   L   L   A   A   A   H   S   A   F   A   A   A   E   H   C   N>
                                          pP67 SIGNAL PEPTIDE
```

FIG.2 pVLgp 120

(Bam H1)
GGATCTCAT ATG AGA GTG AAG GAG AAA TAT CAG CAC TTG TGG AGA TGG GGG TGG AGA TGG GCC ACC ATG CTC CTT GGG ATC TTG ATC ATC TGT AGT GCT ACA GAA
         Met Arg Val Lys Glu Lys Tyr Gln His Leu Trp Arg Trp Gly Trp Arg Trp Gly Thr Met Leu Leu Gly Ile Leu Ile Ile Cys Ser Ala Thr Glu ...

pVLBS1egt 120

(Bam H1)
GGATCTAAT ATG ACT ATC CTT TGC CTG GCC CTT CTG TCA ACT CTG ACT GCC GTC AAC GCT GCC GTA CTG ACA GAA
         Met Thr Ile Leu Cys Trp Leu Ala Leu Leu Ser Thr Leu Thr Ala Val Asn Ala Ala Val Leu Thr Glu ...

pVLBSp67 120

(Bam H1)
GGATC ATG GTA AGC GCT ATT GTT TTA TAT GTG CTT TTG GCC GCC GCG GCG GCG CAT TCT GCC TTT GCG GAG CAC TGC AAC GGG ATC ACA GAA
      Met Val Ser Ala Ile Val Leu Tyr Val Leu Leu Ala Ala Ala Ala Ala His Ser Ala Phe Ala Glu His Cys Asn Gly Ile Thr Glu ...

FIG.7

Medium

Cells

SEQUENCE LISTING ( 1 ) GENERAL INFORMATION:

( i i i ) NUMBER OF SEQUENCES: 19

( 2 ) INFORMATION FOR SEQ ID NO:1:

( i ) SEQUENCE CHARACTERISTICS:
        ( A ) LENGTH: 57 base pairs (B) TYPE: nucleic acid
(C) STRANDEDNESS: both
(D) TOPOLOGY: linear (xi) SEQUENCE DESCRIPTION: SEQ ID NO:1:

ATGACTATTC TCTGCTGGCT TGCACTGCTG TCTACGCTTA CTGCTGTAAA TGCGGCC    57

(2) INFORMATION FOR SEQ ID NO:2:

(i) SEQUENCE CHARACTERISTICS:
 (A) LENGTH: 69 base pairs
 (B) TYPE: nucleic acid
 (C) STRANDEDNESS: both
 (D) TOPOLOGY: linear (ix) FEATURE:
 (A) NAME/KEY: CDS
 (B) LOCATION: 9..68

(xi) SEQUENCE DESCRIPTION: SEQ ID NO:2:

```
GATCTAAT ATG ACT ATC CTT TGC TGG CTG GCC CTT CTG TCA ACT CTG ACT    50
         Met Thr Ile Leu Cys Trp Leu Ala Leu Leu Ser Thr Leu Thr
          1           5                  10

GCC GTC AAC GCT GCG GTA C                                            69
Ala Val Asn Ala Ala Val
 15              20
```

(2) INFORMATION FOR SEQ ID NO:3:

(i) SEQUENCE CHARACTERISTICS:
 (A) LENGTH: 20 amino acids
 (B) TYPE: amino acid
 (D) TOPOLOGY: linear (ii) MOLECULE TYPE: protein (xi) SEQUENCE DESCRIPTION: SEQ ID NO:3:

```
Met Thr Ile Leu Cys Trp Leu Ala Leu Leu Ser Thr Leu Thr Ala Val
 1           5                  10                  15

Asn Ala Ala Val
          20
```

(2) INFORMATION FOR SEQ ID NO:4:

(i) SEQUENCE CHARACTERISTICS:
 (A) LENGTH: 100 base pairs
 (B) TYPE: nucleic acid
 (C) STRANDEDNESS: both
 (D) TOPOLOGY: linear (ix) FEATURE:
 (A) NAME/KEY: CDS
 (B) LOCATION: 5..79

(xi) SEQUENCE DESCRIPTION: SEQ ID NO:4:

```
GATC ATG GTA AGC GCT ATT GTT TTA TAT GTG CTT TTG GCG GCG GCG GCG       49
     Met Val Ser Ala Ile Val Leu Tyr Val Leu Leu Ala Ala Ala Ala
      1           5                  10                  15

CAT TCT GCC TTT GCG GCG GAG CAC TGC AAC GGATCCTAAG TAGGTAGGTAC        100
His Ser Ala Phe Ala Ala Glu His Cys Asn
             20                  25
```

(2) INFORMATION FOR SEQ ID NO:5:

(i) SEQUENCE CHARACTERISTICS:
 (A) LENGTH: 25 amino acids
 (B) TYPE: amino acid
 (D) TOPOLOGY: linear (ii) MOLECULE TYPE: protein (xi) SEQUENCE DESCRIPTION: SEQ ID NO:5:

```
Met Val Ser Ala Ile Val Leu Tyr Val Leu Leu Ala Ala Ala Ala His
 1               5                  10                  15
Ser Ala Phe Ala Ala Glu His Cys Asn
            20                  25
```

(2) INFORMATION FOR SEQ ID NO:6:

(i) SEQUENCE CHARACTERISTICS:
        (A) LENGTH: 101 base pairs
        (B) TYPE: nucleic acid
        (C) STRANDEDNESS: both
        (D) TOPOLOGY: linear (ix) FEATURE:
        (A) NAME/KEY: CDS
        (B) LOCATION: 5..82

(xi) SEQUENCE DESCRIPTION: SEQ ID NO:6:

```
GATC ATG GTA AGC GCT ATT GTT TTA TAT GTG CTT TTG GCG GCG GCG GCG         49
     Met Val Ser Ala Ile Val Leu Tyr Val Leu Leu Ala Ala Ala Ala
      1               5                  10                  15

CAT TCT GCC TTT GCG GCG GAG CAC TGC AAC GGG ATCCTAAGTA GGTAGGTAC        101
His Ser Ala Phe Ala Ala Glu His Cys Asn Gly
               20                  25
```

(2) INFORMATION FOR SEQ ID NO:7:

(i) SEQUENCE CHARACTERISTICS:
        (A) LENGTH: 26 amino acids
        (B) TYPE: amino acid
        (D) TOPOLOGY: linear (ii) MOLECULE TYPE: protein (xi) SEQUENCE DESCRIPTION: SEQ ID NO:7:

```
Met Val Ser Ala Ile Val Leu Tyr Val Leu Leu Ala Ala Ala Ala His
 1               5                  10                  15
Ser Ala Phe Ala Ala Glu His Cys Asn Gly
            20                  25
```

(2) INFORMATION FOR SEQ ID NO:8:

(i) SEQUENCE CHARACTERISTICS:
        (A) LENGTH: 102 base pairs
        (B) TYPE: nucleic acid
        (C) STRANDEDNESS: both
        (D) TOPOLOGY: linear (ix) FEATURE:
        (A) NAME/KEY: CDS
        (B) LOCATION: 5..82

(xi) SEQUENCE DESCRIPTION: SEQ ID NO:8:

```
GATC ATG GTA AGC GCT ATT GTT TTA TAT GTG CTT TTG GCG GCG GCG GCG         49
     Met Val Ser Ala Ile Val Leu Tyr Val Leu Leu Ala Ala Ala Ala
      1               5                  10                  15

CAT TCT GCC TTT GCG GCG GAG CAC TGC AAC GGG GATCCTAAGT AGGTAGGTAC       102
His Ser Ala Phe Ala Ala Glu His Cys Asn Gly
               20                  25
```

(2) INFORMATION FOR SEQ ID NO:9:

(i) SEQUENCE CHARACTERISTICS:
        (A) LENGTH: 26 amino acids
        (B) TYPE: amino acid ( D ) TOPOLOGY: linear ( i i ) MOLECULE TYPE: protein ( x i ) SEQUENCE DESCRIPTION: SEQ ID NO:9:

```
Met Val  Ser Ala Ile Val Leu Tyr Val Leu Leu Ala Ala Ala Ala His
 1               5                  10                      15
Ser Ala Phe Ala Ala Glu His Cys Asn Gly
            20                  25
```

( 2 ) INFORMATION FOR SEQ ID NO:10:

( i ) SEQUENCE CHARACTERISTICS:
        ( A ) LENGTH: 39 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:10:

TGACAGAAAA ATTGTGGGTC ACAGTCTATT TTGGGGTAC        39

( 2 ) INFORMATION FOR SEQ ID NO:11:

( i ) SEQUENCE CHARACTERISTICS:
        ( A ) LENGTH: 39 base pairs
        ( B ) TYPE: nucleic acid
        ( C ) STRANDEDNESS: both
        ( D ) TOPOLOGY: linear ( x i ) SEQUENCE DESCRIPTION: SEQ ID NO:11:

CCCAAAATAG ACTGTGACCC ACAATTTTTC TGTCAGTAC        39

( 2 ) INFORMATION FOR SEQ ID NO:12:

( i ) SEQUENCE CHARACTERISTICS:
        ( A ) LENGTH: 27 base pairs
        ( B ) TYPE: nucleic acid
        ( C ) STRANDEDNESS: both
        ( D ) TOPOLOGY: linear ( x i ) SEQUENCE DESCRIPTION: SEQ ID NO:12:

GGCCTGATCA CAGAAAAATT GTGGGTC        27

( 2 ) INFORMATION FOR SEQ ID NO:13:

( i ) SEQUENCE CHARACTERISTICS:
        ( A ) LENGTH: 24 base pairs
        ( B ) TYPE: nucleic acid
        ( C ) STRANDEDNESS: both
        ( D ) TOPOLOGY: linear ( x i ) SEQUENCE DESCRIPTION: SEQ ID NO:13:

CCGGCCTCCT CTTCAGCAGA GTCG        24

( 2 ) INFORMATION FOR SEQ ID NO:14:

( i ) SEQUENCE CHARACTERISTICS:
        ( A ) LENGTH: 105 base pairs
        ( B ) TYPE: nucleic acid
        ( C ) STRANDEDNESS: both
        ( D ) TOPOLOGY: linear ( i x ) FEATURE:
        ( A ) NAME/KEY: CDS
        ( B ) LOCATION: 10..105

( x i ) SEQUENCE DESCRIPTION: SEQ ID NO:14:

GGATCTCAT ATG AGA GTG AAG GAG AAA TAT CAG CAC TTG TGG AGA TGG        48

```
                Met  Arg  Val  Lys  Glu  Lys  Tyr  Gln  His  Leu  Trp  Arg  Trp
                 1              5                        10

GGG  TGG  AGA  TGG  GGC  ACC  ATG  CTC  CTT  GGG  ATG  TTG  ATG  ATC  TGT  AGT              96
Gly  Trp  Arg  Trp  Gly  Thr  Met  Leu  Leu  Gly  Met  Leu  Met  Ile  Cys  Ser
      15                        20                        25

GCT  ACA  GAA                                                                               105
Ala  Thr  Glu
 30
```

( 2 ) INFORMATION FOR SEQ ID NO:15:

( i ) SEQUENCE CHARACTERISTICS:
        ( A ) LENGTH: 32 amino acids
        ( B ) TYPE: amino acid
        ( D ) TOPOLOGY: linear ( i i ) MOLECULE TYPE: protein ( x i ) SEQUENCE DESCRIPTION: SEQ ID NO:15:

```
Met  Arg  Val  Lys  Glu  Lys  Tyr  Gln  His  Leu  Trp  Arg  Trp  Gly  Trp  Arg
 1              5                        10                       15

Trp  Gly  Thr  Met  Leu  Leu  Gly  Met  Leu  Met  Ile  Cys  Ser  Ala  Thr  Glu
                20                        25                       30
```

( 2 ) INFORMATION FOR SEQ ID NO:16:

( i ) SEQUENCE CHARACTERISTICS:
        ( A ) LENGTH: 78 base pairs
        ( B ) TYPE: nucleic acid
        ( C ) STRANDEDNESS: both
        ( D ) TOPOLOGY: linear ( i x ) FEATURE:
        ( A ) NAME/KEY: CDS
        ( B ) LOCATION: 10..78

( x i ) SEQUENCE DESCRIPTION: SEQ ID NO:16:

```
GGATCTAAT  ATG  ACT  ATC  CTT  TGC  TGG  CTG  GCC  CTT  CTG  TCA  ACT  CTG        48
           Met  Thr  Ile  Leu  Cys  Trp  Leu  Ala  Leu  Leu  Ser  Thr  Leu
            1              5                        10

ACT  GCC  GTC  AAC  GCT  GCG  GTA  CTG  ACA  GAA                                    78
Thr  Ala  Val  Asn  Ala  Ala  Val  Leu  Thr  Glu
      15                        20
```

( 2 ) INFORMATION FOR SEQ ID NO:17:

( i ) SEQUENCE CHARACTERISTICS:
        ( A ) LENGTH: 23 amino acids
        ( B ) TYPE: amino acid
        ( D ) TOPOLOGY: linear ( i i ) MOLECULE TYPE: protein ( x i ) SEQUENCE DESCRIPTION: SEQ ID NO:17:

```
Met  Thr  Ile  Leu  Cys  Trp  Leu  Ala  Leu  Leu  Ser  Thr  Leu  Thr  Ala  Val
 1              5                        10                       15

Asn  Ala  Ala  Val  Leu  Thr  Glu
                20
```

( 2 ) INFORMATION FOR SEQ ID NO:18:

( i ) SEQUENCE CHARACTERISTICS:
        ( A ) LENGTH: 92 base pairs
        ( B ) TYPE: nucleic acid
        ( C ) STRANDEDNESS: both
        ( D ) TOPOLOGY: linear ( i x ) FEATURE:

(A) NAME/KEY: CDS
(B) LOCATION: 6..92

(xi) SEQUENCE DESCRIPTION: SEQ ID NO:18:

```
GGATC ATG GTA AGC GCT ATT GTT TTA TAT GTG CTT TTG GCG GCG GCG       47
      Met Val Ser Ala Ile Val Leu Tyr Val Leu Leu Ala Ala Ala
      1               5                   10

GCG CAT TCT GCC TTT GCG GCG GAG CAC TGC AAC GGG ATC ACA GAA          92
Ala His Ser Ala Phe Ala Ala Glu His Cys Asn Gly Ile Thr Glu
15                  20                  25
```

(2) INFORMATION FOR SEQ ID NO:19:

(i) SEQUENCE CHARACTERISTICS:
      (A) LENGTH: 29 amino acids
      (B) TYPE: amino acid
      (D) TOPOLOGY: linear (ii) MOLECULE TYPE: protein (xi) SEQUENCE DESCRIPTION: SEQ ID NO:19:

```
Met Val Ser Ala Ile Val Leu Tyr Val Leu Leu Ala Ala Ala Ala His
1               5                   10                  15

Ser Ala Phe Ala Ala Glu His Cys Asn Gly Ile Thr Glu
            20                  25
```

BACULOVIRUS VECTORS FOR EXPRESSION OF SECRETORY AND MEMBRANE-BOUND PROTEINS

U.S. GOVERNMENT LICENSE RIGHTS

The U.S. Government has a paid-up license in this invention and the right in limited circumstances to require the patent owner to license others on reasonable terms as provided for by the terms of Grant No. AI 27135 awarded by the National Institutes of Health.

CROSS-REFERENCE TO RELATED APPLICATIONS

This application is a continuation-in-part of U.S. application Ser. No. 07/880,647, filed May 11, 1992, now abandoned which disclosure is hereby incorporated in its entirety.

FIELD OF THE INVENTION

This invention broadly relates to recombinant DNA technology. More specifically, this invention relates to the use of vector technology as it may be applied to the expression of recombinant proteins. In particular, the invention is directed to the use of Baculovirus vectors to express recombinant proteins during Baculovirus infection.

BACKGROUND OF THE INVENTION

The use of recombinant Baculoviruses as expression vectors is well known. Typically, the use of recombinant Baculovirus vectors involves the construction and isolation of recombinant Baculoviruses in which the coding sequence for a chosen gene is inserted behind the promoter for a nonessential viral gene, polyhedrin. A number of Baculovirus expression vectors based on the polyhedrin promoter have been previously described. Smith et al., Mol. Cell. Biol. 3:2156–2165 (1985); Posse, Virus Res. 5:43–59 (1986); and Matsuura, J. Gen. Virol. 68:1233–1250 (1987).

One advantage of the Baculovirus vectors over bacterial and yeast expression vectors includes the expression of recombinant proteins that are essentially authentic and are antigenitally and/or biologically active. In addition, Baculoviruses are not pathogenic to vertebrates or plants and do not employ transformed cells or transforming elements as do the mammalian expression systems. Although mammalian expression systems result in the production of fully modified, functional protein, yields are often low. E. coli systems result in high yields of recombinant protein but the protein is not modified and may be difficult to purify in a nondenatured state.

The usual host cell for a Baculovirus vector is Sf9, a clonal isolate established from Spodoptera frugiperda, commonly known as the fall army worm. Usually, the use of a Baculovirus vector in combination with Sf9 results in the production of proteins that are essentially authentic and are antigenitally and/or biologically active. Expression in Baculovirus-infected insect cells has the advantage of generating large amounts of protein closely related to its native counterpart and is often much easier to purify. However, further investigations have suggested that the Sf9 cells and mammalian cells exhibit some differences in the basic mechanism of protein glycosylation. In particular, one major difference between recombinant proteins produced in insect cells and those derived from mammalian cells is the extent and type of oligosaccharide processing.

Sf9 cells used for Baculovirus expression are capable of adding N-glycosylated carbohydrate chains to proteins and in some cases process them to an endo-H-resistant form.

The addition of carbohydrate to a protein is important because carbohydrate often plays a major role in the overall structure and function of a protein. More specifically, carbohydrates are responsible for blood group antigenicity, controlling events in growth and differentiation, and they also contribute to the protection of proteins from degradation. In addition, oligosaccharides may maintain protein conformation in a biologically active state.

There are several examples in the literature of proteins that are glycosylated or secreted efficiently early in virus infection (24 hours p.i.), but fail to be glycosylated or secreted late in infection (after 48 hours p.i.) when the polyhedrin promoter of the Baculovirus vector is most active. Murphy et al., Gen. Anal. Tech. Appl. 7:160–171 (1990); Jarvis et al., Mol. Cell. Biol. 9:214–223 (1989); and Bailey et al., Virology 169:323–331 (1989). In these uses, poor yields of recombinant product were obtained compared with the amount of polyhedrin produced in wild type Baculovirus infection. For example, Jarvis et al. examined the pathway of protein glycosylation and secretion in Sf9 cells using human tissue plasminogen activator (TPA) as a model. Although Jarvis et al. report that the TPA expressed by Sf9 was both N-glycosylated and secreted, the relative efficiency of secretion decreased dramatically with time of infection. Jarvis et al.'s results led them to conclude that the Sf9 host cell secretory pathway is therefore somehow compromised during the later stages of Baculovirus infection.

A need therefore exists for a Baculovirus vector that will allow for the production of proteins that are glycosylated and secreted in the late term of infection when its promoter is most active.

Some success in increasing yields of proteins directed to the endoplasmic reticulum has been obtained by manipulating the signal peptide of the recombinant protein. When the honeybee mellitin signal peptide was fused to the plant papain precursor it was secreted over five times more than the wild type protein containing the plant signal peptide (Tessier et al., Gene 98:177–183 (1991)). However, the use of a consensus signal peptide based on a survey of eukaryotic signal peptides by von Heijne (von Heijne, G., Nucl. Acids Res. 11:4683–4691 (1986)) did not result in significantly more secretion of chimeric plasminogen activator proteins (Devlin, J. J., et al., Biotechnology 7:286–292 (1989)). This application describes the construction of two secretion vectors containing the egt and p67 signal peptides and the use of these vectors to express and secrete the HIV-1 gp120 protein from insect cells.

SUMMARY OF THE INVENTION

The present invention provides a Baculovirus vector that contains a polyhedrin promoter upstream from a signal peptide coding region that is derived from a Baculovirus protein. The signal peptide allows a recombinant protein to be glycosylated or secreted late in infection because the recombinant protein is efficiently processed through the host cell's endoplasmic reticulum.

Several Baculovirus proteins that may be used to obtain the signal peptides of the present invention have been identified. For example, one signal peptide is encoded by the Autographa californica nuclear polyhedrosis virus (AcMNPV) egt gene. This gene encodes the 60 kilodalton (kd) signal peptide-containing ecdysteriod UDP-glucosyltransferase, which is secreted by virus-infected insect cells. O'Reilly et al., *Science* 245:1110–1112 (1989); and O'Reilly et al., *J. Virol.* 64:1321–1328 (1990). A second signal peptide is derived from the glycoprotein p67, which is an acidic protein present on the surface of AcMNPV particles. Whitford et al., *J. Virol.* 63:1393–1399 (1989). Both of the genes encoding these proteins have been cloned and sequenced.

In addition, the invention provides a method for making *Baculovirus* vectors comprising a promoter upstream from a signal peptide which is upstream from a DNA sequence encoding a protein.

The invention further includes a method for expressing a recombinant protein that will be expressed in the late term of infection using a *Baculovirus* vector. This method comprises providing the above described *Baculovirus* vector containing a promoter, a peptide signal and a protein gene, generating a recombinant virus and infecting a host cell with the recombinant virus such that the desired protein is expressed.

DESCRIPTION OF FIGURES

FIG. 1 is the DNA sequence [SEQ ID No. 2] and amino acid sequence [SEQ ID No 3] for the egt signal peptide. The underlined nucleotides are those which differ from the published authentic sequence.

FIG. 2 represents the three p67 oligonucleotide sequences [SEQ. ID NO: 4,5,6,7,8,9] that may also be used as the signal peptide of the present invention.

FIG. 7 shows DNA sequences of the 5' coding regions of the gp120 baculovirus transfer vectors pVLgp120 [SEQ ID No. 14], pVLBS1egt120 [SEQ ID No. 16], and pVLBS2p67120 [SEQ ID No. 18]. The amino acid sequences corresponding to pVLgp120 [SEQ ID No. 15], pVLBS1egt120 [SEQ ID No. 17], and pVLBS2p67120 [SEQ ID No. 19], shown underneath the DNA sequences, contain the complete signal peptide sequences, the predicted cleavage sites for the signal peptide indicated by an arrow, and the start of the mature gp120 protein (underlined). The BamH I sites shown in parentheses refer to the original BamH I site from pVL941.

FIG. 8A: medium samples; FIG. 8B: NP40 soluble cell extract samples. Molecular weight markers (in kilodaltons) are indicated on the left.

DEFINITIONS

Figure 3:
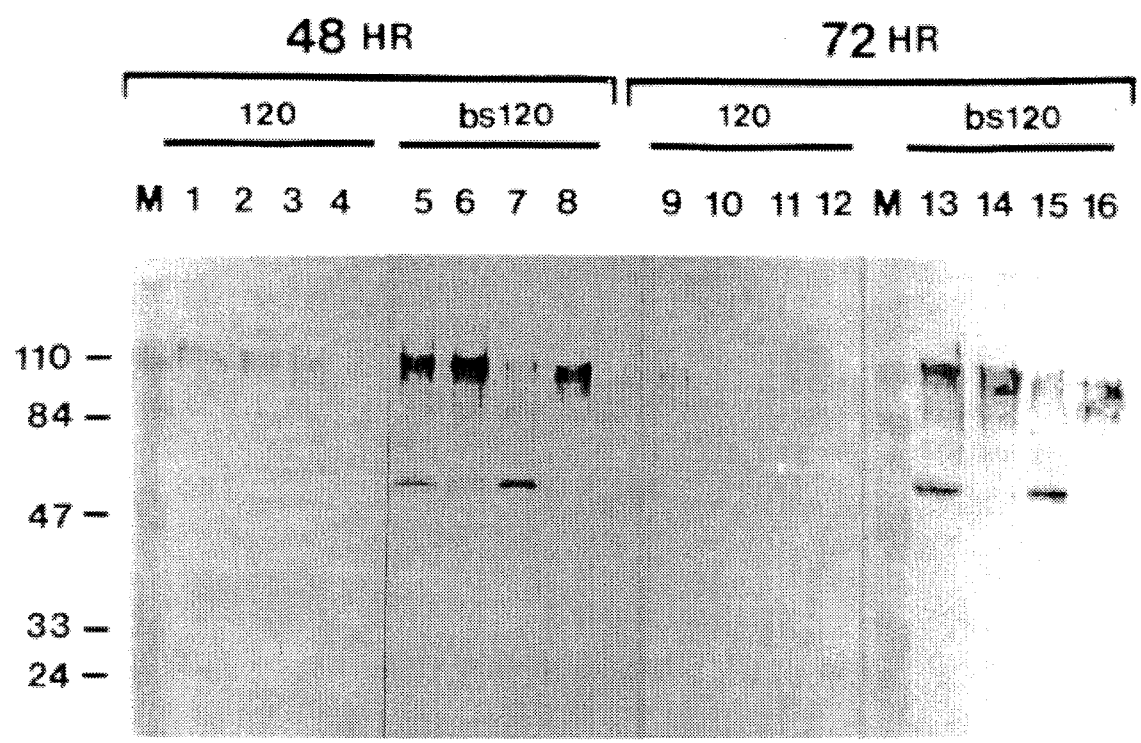
FIG. 3 represents the Western blot obtained by following the procedure of Example 1.
Figure 4:
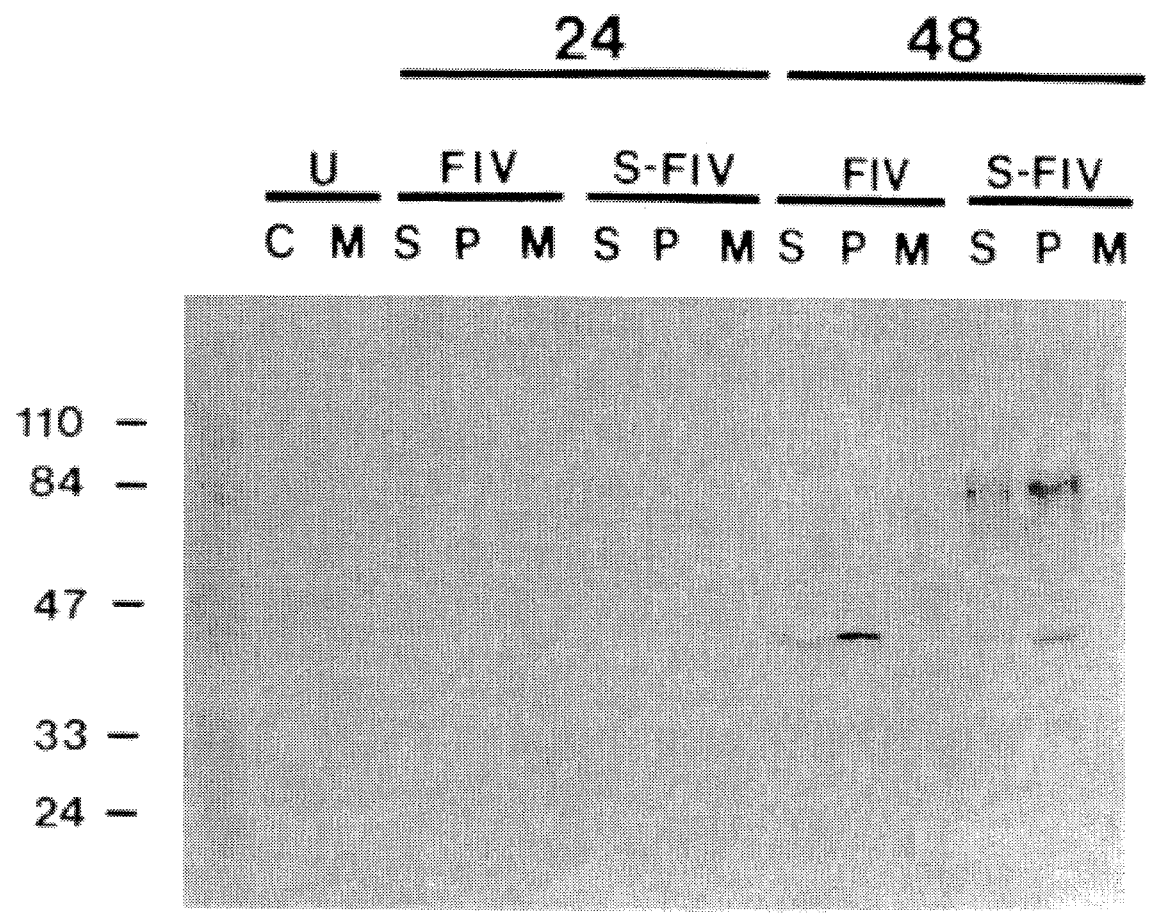
FIG. 4 represents the Western blot obtained by following the procedure of Example 2.
Figure 5:
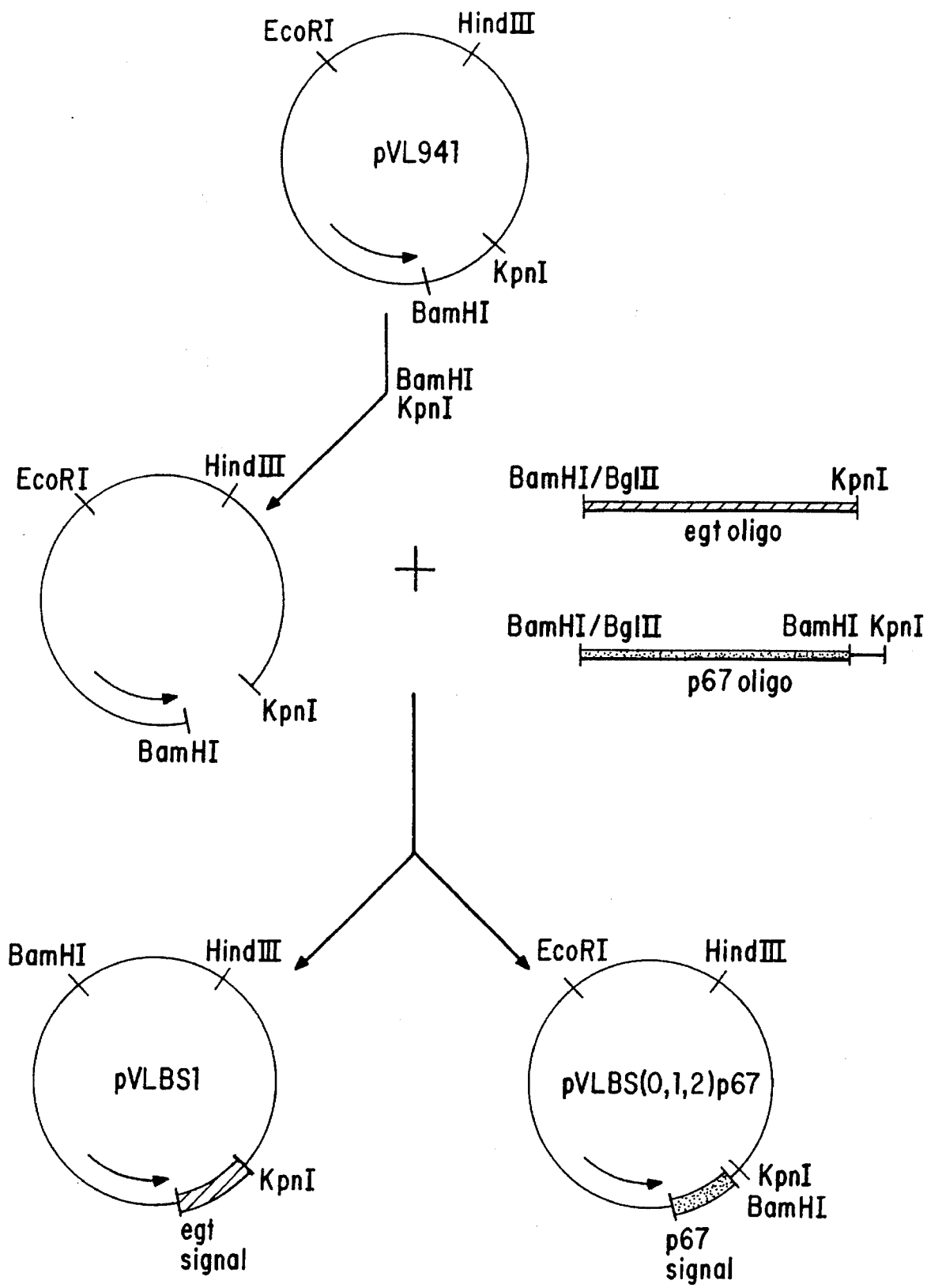
FIG. 5 is the vector construction flow chart for a vector comprising the egt signal sequence and a vector comprising the p67 signal sequence.

By the term "promoter" is intended a DNA sequence at the 5'-end of a structural gene that is capable of initiating transcription. The preferred promoter of the present invention is the promoter for the *Baculovirus* nonessential gene, polyhedrin. Other *Baculovirus* promoters include the p10 promoter and those described by Vialard et al. *J. Virol.* 64:37–50 (1990); and Vlak et al. *Virology* 179:312–320 (1990). In order for the promoter to initiate transcription, the coding sequence for a desired protein must be inserted "downstream," "3'" or "behind" the promoter.

By the term "signal peptide" is intended a sequence of amino acid residues that initiate the transcription of membrane or secreted proteins across the membrane of the endoplasmic reticulum. The preferred signal peptides of the present invention are signal peptides derived from *Baculovirus* proteins. The signal peptides may range in length from 10 to 50 amino acids, preferably 18 to 30 amino acids. Because the genetic code is degenerate, more than one codon may be used to encode a particular amino acid. More specifically, the AcMNPV genome encodes a 60 kd ecdysteroid UDP-glucosyltransferase which is secreted by virus-infected insect cells, and the glycoprotein p67 which is an acidic protein present on the surface of AcMNPV particles. See Whitford et at., *J. Virol.* 63:1393–1399 (1989). The "signal peptides" of the present invention, may or may not be cleaved prior to membrane insertion or secretion.

The term "operably linked" is intended to refer to two sequences of a nucleic acid molecule which are linked to each other in a manner which either permits both sequences to be transcribed onto the same RNA transcript, or permits an RNA transcript, begun in one sequence, to be extended into the second sequence. Thus, two sequences, such as a promoter and any other "second" sequence of DNA (or RNA) are operably linked if transcription commencing in the promoter sequence will produce an RNA (or cDNA) transcript of the operably linked second sequence. In order to be "operably linked" it is not necessary that two sequences be immediately adjacent to one another.

By the term "transforming" is intended the act of causing a cell to contain a nucleic acid molecule or sequence not originally part of that cell. This is the process by which DNA is introduced into a cell. Methods of transformation are known in the art. See e.g., Maniatis et al., *Molecular Cloning: A Laboratory Manual*, (Cold Spring Harbor Laboratory, Publisher, N.Y. (2d ed. 1989).

By the term "transfecting" is intended the introduction of viral DNA or RNA into any cell.

By the term "vector" is intended a DNA element used as a vehicle for cloning or expressing a fragment of foreign DNA.

By the term "host" or "host cell" is intended the cell in which a vector is transformed. Once the foreign DNA is incorporated into the host cell, the host cell may express the foreign DNA. The preferred "host cell" of the present invention is Sf9, a clonal isolate of the IPLB-Sf21-AE line established from *Spodoptera frugiperda*, commonly known as the fall army worm. Vaughn et al. *In Vitro* (Rockville) 13:213–217 (1977).

By the phrase "in the late term of infection" is intended a time period in which the polyhedrin promoter of the *Baculovirus* vector is most active, usually more than 24 hours after a host cell has been infected with *Baculovirus*.

By the phrase "in the early term of infection" is intended the time period from 0 to 24 hours after a host cell has been infected with *Baculovirus*.

By the term "glycosylate" or "glycosylation" is intended a protein that contains one or more carbohydrate groups.

By the term "fusion" is intended a protein in combination with a signal peptide that has been secreted, such as membrane bound proteins.

By the phrase "in phase" or "correct reading frame" is meant that the nucleotide sequence of interest is in the same reading frame as those nucleotide sequences to which the sequence of interest may be operably linked.

By the term "derived" is intended something, such as for example a peptide, that may be produced by modification of something already existing, such as for example a protein.

By the term "derivative" is intended a modified peptide or protein due to codon modifications which yield the same amino acid. See Watson, J. D., In: *Molecular biology of the Gene*, 3rd ed., W. A. Benjamin, Inc., Menlo Park, Calif. (1977), pp. 356–57. "Derivatives" may be tested for use by one of skill in the art by insertion into the *Baculovirus* system detailed herein.

DETAILED DESCRIPTION OF THE INVENTION

This invention is based upon the discovery that a *Baculovirus* vector may be used to glycosylate and secrete a protein during the *Baculovirus* infection of the host cell. The inventive *Baculovirus* vector, comprised of a promoter upstream from a signal peptide, is particularly useful and advantageous to the biotech community because it allows a protein to be glycosylated and secreted; and it expresses the glycosylated proteins at levels higher than previously obtainable. The glycosylated and secreted proteins, including membrane bound proteins, and fusions, may then be used for any use known to proteins.

A preferred embodiment of the *Baculovirus* vector comprises a polyhedrin promoter upstream from a *Baculovirus* protein-derived signal peptide.

The polyhedrin promoter is a *Baculovirus* promoter that naturally promotes the nonessential vital gene, polyhedrin. *Baculovirus* vectors containing the polyhedrin promoter are described by Smith et al., *Mol. Cell. Biol.* 3:2156–2165 (1985); Posse, *Virus Res.* 5:43–59 (1986); and Matsuura, *J. Gen. Virol.* 68:1233–1250 (1987); all of which are incorporated herein by reference.

The preferred signal peptides of the present invention are derived from *Baculovirus* proteins. In particular, the preferred signal peptides are derived from any AcMNPV derived protein. The nucleotide sequence for the egt signal peptide is represented by FIG. 7 [SEQ ID NO: 16, 17]. The p67 oligonucleotide sequences are shown in FIG. 7 [SEQ ID NO: 14, 15, 16, 17, 18, 19]. Due to the degenerative nature of the genetic code, modifications of these signal peptides can be made by altering one or more codon for a particular amino acid. Other signal peptides include those derived from honeybee melittin (Tesslet et al., *Gene* 98:177–183 (1991), or the "consensus" signal peptides described by Devlin et al., *Biotechnology* 7:286–92 (1989).

Once a *Baculovirus* vector comprised of a promoter and a signal peptide has been constructed, the gene for the desired protein may be inserted into the vector downstream from the signal peptide. More specifically, the signal peptides of the present invention can be designed to contain appropriate restriction sites, so that foreign genes can be inserted thereinto. For example, certain signal peptides of the present invention have been designed to have a BamH I or a Kpn I site for foreign gene insertion. The use of restriction endonucleases and associated molecular biology techniques needed to construct the vectors of the present invention are described in Maniatis et al., *Molecular Cloning: A Laboratory Manual*, Cold Spring Harbor Laboratory, Publisher, N.Y. (2d ed. 1989).

The foreign gene encoding any protein, peptide hormone, interleukin, or peptide may be inserted into the vector. For example, the following nonexclusive list of proteins that may be expressed include: Human immunodeficiency virus type 1 or 2 envelope proteins and derivatives; Human T-cell leukemia virus type 1 or 2 envelope proteins and derivatives; Feline leukemia virus envelope proteins; Feline immunodeficiency virus envelope proteins; Simian immunodeficiency virus envelope proteins; Hepatitis A, B or C proteins; Adenovirus proteins; Rotavirus proteins; Parvovirus proteins; Influenza virus proteins; Polio virus proteins; Human t-PA; Rabies virus proteins; Rubella virus proteins; Human growth factor receptors; Human erythropoietin; Human glucocerebrosidase; Herpes virus proteins; Human hormones; human interleukins; Human blood factors; and Human cell surface proteins.

Recombinant virus may be generated by transfecting wild-type virus and the *Baculovirus* vector into Sf9 cells. See Summers and Smith, *Texas Agri. Experimental Station Bulletin* No. 1555 (1987). Wild-type viruses that may be used to generate a recombinant virus include the *Baculoviruses Autographa Californica* MNPV, *Bombyx Mori* MNPV, and *Heliothis zea* SNPV.

The recombinant virus can then be used to infect a host cell, such as, for example, Sf9. Sf9 cells are typically infected with recombinant virus by placing Sf9 cells in a flask and infecting the cells with a quantity of virus, for example, a multiplicity of infection of 10 plaque-forming units per cell with recombinant virus. The infected cells are then propagated on growth medium, for example, 5 ml of Grace medium containing 10% of heat-inactivated fetal bovine serum and antibiotics. Other growth mediums are specified in Broussard et al. *J. Invert. Pathol.* 54:144–150 (1989); and Summers and Smith, *Texas Agri. Experimental Station Bulletin* No. 1555 (1987). Serum free insect cell media are also available from Gibco BRL, JRH scientific and Hyclone. After expression of the cloned sequences, the proteins would typically be recovered and may be purified according to means known in the art.

The signal peptide-containing *Baculovirus* vectors of the invention are capable of expressing surprisingly high levels of glycosylated proteins. The materials and methods used in carrying out the present invention may be more fully understood by reference to the following examples, which examples are not intended in any manner to limit the scope of the present invention.

EXAMPLES

Example 1

Two sets of oligonucleotides were synthesized containing the DNA coding regions for each of the two signal peptides (egt and p67).

The amino acid sequence from which the DNA sequence for the egt signal peptide was deduced, was that published by O'Reilly et al., *Science* 245:1110–1112 (1989) (see FIG. 1), and differs from the authentic sequence published after this work was done. The underlined nucleotides in FIG. 1 are those which differ from the actual sequence (the authentic egt signal peptide nucleotide sequence is ATG ACT ATT CTC TGC TGG CTT GCA CTG CTG TCT ACG CTT ACT GCT GTA AAT GCG GCC) [SEQ. ID No. 1]. The double stranded oligonucleotide was designed to have a BamHI/Bgl2 compatible 5' end and a Kpn1 compatible 3' end. This DNA was cloned into, the *Baculovirus* vector pVL941 (Luckow and Summers, *Virology* 170:31–39 (1989)) which had been cut with BamHI and Kpn1. The resulting clone, pVLBS1, contains the coding region for the egt signal peptide under the control of the polyhedrin promoter. Foreign genes can be inserted at the Kpn1 site after ensuring that the correct reading frame is preserved.

The egt cloning vector was tested using the gp120 protein from HIV-1. After removing the HIV-1 signal peptide coding region the gp120 gene was cloned in frame downstream of the egt signal peptide cloning region. The resulting DNA contained nucleotides 5894–7335 derived from the BH8 isolate of HIV-1 (Ratner et at., *Nature* 313:277–284 (1985)). Recombinant virus (BS120) containing the HIV-1 gp120 DNA was generated using the procedures of Summers and Smith *Texas Agri. Experimental Station Bulletin* No. 1555 (1987).

Protein expression and secretion were analyzed in infected Sf9 cells using the BS120 virus and a recombinant virus containing the HIV-1 120 gene and the HIV-1 envelope signal peptide coding region (Murphy et al., *Gen. Anal. Tech. Appl.* 7:160–171 (1990)). Two shake flasks containing 20 ml each of Sf9 cells at $1\times10^6$ cells per ml were infected with gp120 virus and BS120 virus at a multiplicity of infection (MOI) of 10. Infected cells were harvested at 48 and 72 hours post-infection (p.i.) and fractionated into whole cell, NP40 soluble, and NP40 insoluble fractions. Aliquots of each fraction plus an aliquot of the culture medium were removed and analyzed. The cells were spun down and the medium was removed. The cells were resuspended in 400 μl NP40 extraction buffer and an aliquot was removed for a whole cell sample. The remainder was incubated at 4° C. for 15 minutes with rocking. The insoluble material was spun out and the soluble fraction removed. One hundred μl PBS was added to the pellets. Equal volumes of Laemmli buffer were added to all fractions and the culture medium before treatment at 100° C. and gel electrophoresis. Proteins were transferred to nitrocellulose for Western blotting and probed with a monoclonal antibody against HIV-1 gp120. See FIG. 3. M: molecular weight markers in kilodaltons, lanes 1, 5, 9, 13: whole cell samples, lanes 2, 6, 10, 14:NP40 soluble samples, lanes 3, 7, 11, 15: insoluble pellet samples, lanes 4, 8, 12, 16: culture medium.

The results show that overall expression of gp120 is much higher in the *Baculovirus* secretion version of gp120. While a small amount of gp120 can be detected in the culture medium at 72 hours (lane 12) using the 120 virus, much more gp120 is present in the medium using the BS120 virus, both at 48 hours and 72 hours p.i. (lanes 8 and 16). Subsequent experiments have shown that 10 to 20 mg per liter of gp120 is secreted into the culture medium using a 5 liter airlift fermenter and the BS120 virus (dam not shown). In comparison, a *Drosophila* expression system yielded only 1 to 2 mg per liter of gp120 (Culp et al., *Biotechnology* 9:173–177 (1991)).

Example 2

The p67 oligonucleotide sequences are shown in FIG. 2. Three sets of oligonucleotides were synthesized, each representing one of the possible three reading frames. All oligonucleotides have a BamHI/Bgl2 compatible 5' end and a Kpn1 compatible 3' end. An internal BamHI site serves as the insertion site for foreign genes and this is followed by termination codons. These oligonucleotides were cloned into pVL941 cut with BamHI and Kpn1. The resulting clones, pVLBS0p67, pVLBS1p67, and pVLBS2p67, are also under the control of the polyhedrin promoter.

The p67 cloning vector, pVLBS2p67, was used to express a portion of the FIV envelope region derived from the Bangston strain of FIV (pVLBS2FIV1.2). This region includes all of the major glycoprotein (gp120 equivalent) minus approximately forty amino acids from the amino terminus. Sf9 cells were grown in 100 ml spinner flasks and infected at an MOI of 10 with BS2FIV1.2 (S-FIV), or FIV1.2 (FIV). The expression of protein was compared to the expression of the same FIV construct cloned into pVL941, a vector without a signal peptide coding region (pVLFIV1.2).

At 24 and 48 hours p.i. one ml aliquots were removed and analyzed. The samples were treated as described in Example 1. The samples were then analyzed by SDS-polyacrylamide gel electrophoresis and Western blotting using a monoclonal antibody directed against the FIV envelope (molecular weight markers are indicated on the left side of FIGS. 3 and 4.) FIG. 4 shows a Western blot of NP40 soluble (S lanes), NP40 insoluble (P lanes) and medium (M lanes) fractions at 24 and 48 hours p.i. for both FIV recombinant viruses. The cells infected with virus derived from pVLBS2FIV1.2 (S-FIV) contained two immunoreactive bands, one at approximately 47 kilodaltons and the other ranging from 80 to 90 kilodaltons. These molecular weights are consistent with the proteins being nonglycosylated and glycosylated versions of the FIV envelope respectively. Some of the higher molecular weight material was present in the culture medium at 48 hours. This protein migrated at a slightly faster rate than that present in the cell, indicating that the signal peptide was probably cleaved off. Of the total envelope protein produced with this virus about 20% is secreted. Cells infected with the pVLFIV1.2 virus (FIV, FIG. 4) only contained the lower molecular weight protein. Overall expression levels were much lower for FIV compared to S-FIV. These results demonstrate that the p67 *Baculovirus* vector not only enables a protein to be glycosylated and secreted but also enables it to be expressed at a higher level.

Example 3

Materials and Methods

Cells and Viruses

*Spodoptera frugipera* cells (Sf9) and AcMNPV were obtained from Max Summers, Texas A&M University. Standard methods for cell growth and propagation of AcMNPV and methods relating to the use of AcMNPV in the baculovirus expression system were followed according to published procedures (Summers and Smith, *Texas Agricultural Experiment Station Bulletin* 1555 (1987); O'Reilly et al., *Baculovirus Expression Vectors*, W.H. Freeman and Company, New York (1992)). Recombinant viruses were screened and purified by plaque assay. Sf9 cells were maintained and infected in Sf900 II, a serum free medium obtained from GIBCO/BRL.

Construction of Recombinant Plasmids

Figure 6:
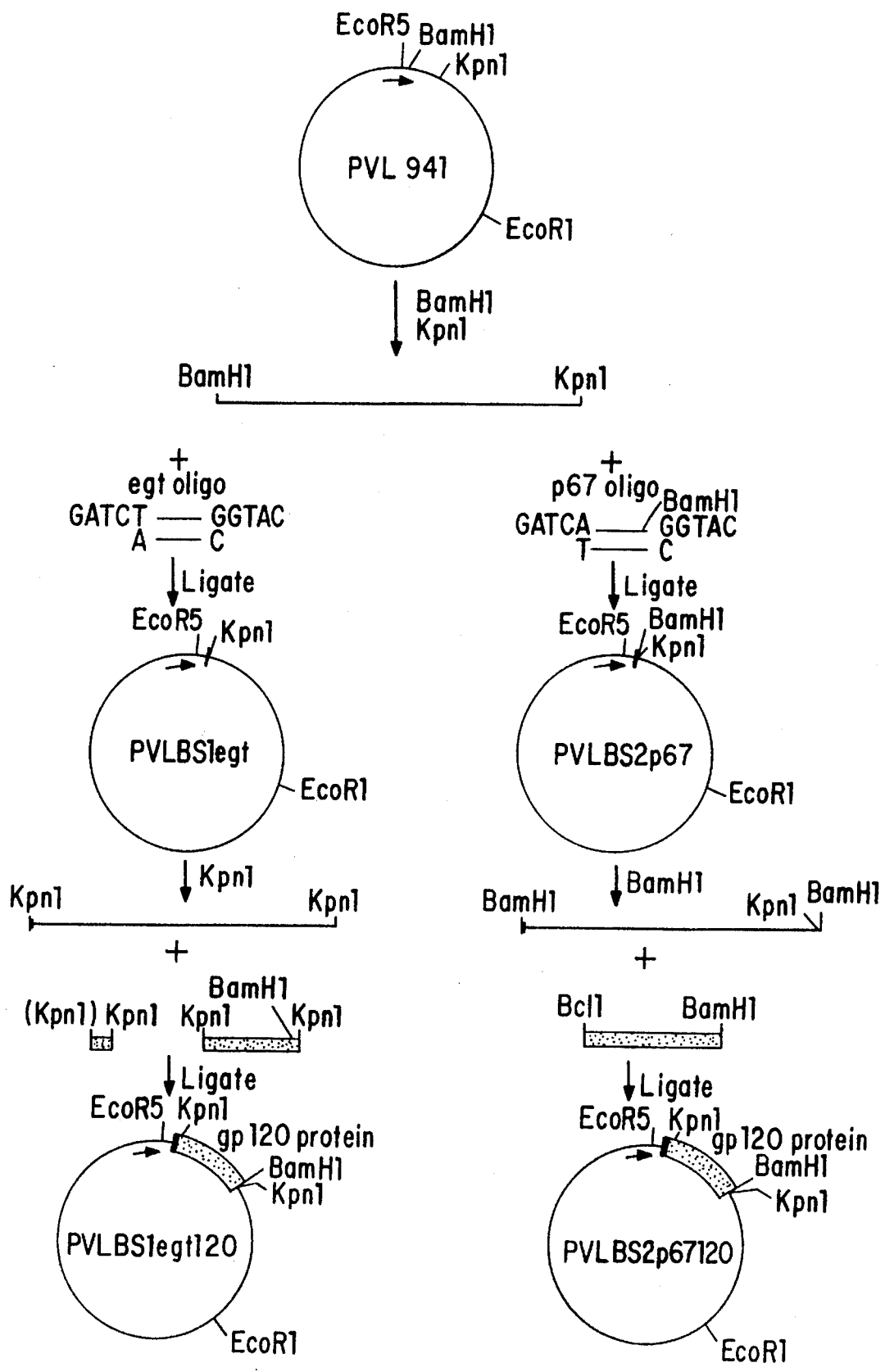
FIG. 6 shows the scheme for the construction of secretion vectors pVLBS1egt and pVLBSp67 and baculovirus transfer vectors containing the HIV-1 gp120 coding region. Restriction enzyme sites that have been altered by cloning are shown in parentheses. In the vectors, the polyhedrin promoter is shown as an arrow. The signal peptide coding regions are shown as solid boxes and the gp120 coding regions are shown as stippled boxes.

Schemes for construction of the baculovirus secretion vectors and the HIV-1 gp120 expression vectors are outlined in FIG. 6. Standard recombinant DNA techniques were used throughout (Sambrook, J. et al., *Molecular Cloning* (2nd ed.), Cold Spring Harbor Laboratory Press, New York (1989)). The baculovirus plasmid pVL941 (Luckow and Summers, *Virology* 170:31–39 (1989)) was obtained from Max Summers, Texas A&M University. The two secretion vectors, pVLBS1egt and pVLBS2p67, were generated by ligating the large BamH I/Kpn I fragment of pVL941 to synthetic oligonucleotides (produced using a Milligen™ DNA synthesizer) containing the signal peptide coding regions from the egt and p67 baculovirus proteins (FIG. 7). Each vector is under the control of the polyhedrin promoter.

The double stranded oligonucleotides used to produce each secretion vector were designed to have a BamH I/Bgl II compatible 5' end and a Kpn I compatible 3' end. The amino acid sequence from which the DNA sequence for the egt signal peptide was deduced, was that published by O'Reilly et al., *Science* 245:1110–1112 (1989) (see FIG. 7 [SEQ ID NO: 16, 17]), and differs from the authentic sequence published after this work was done (The authentic egt signal peptide nucleotide sequence is ATG ACT ATT CTC TGC TGG CTT GCA CTG CTG TCT ACG CTT ACT GCT GTA AAT GCG GCC)[SEQ ID No. 1]. The oligonucleotide containing the p67 sequence also contained an internal BamH I site as the insertion site for foreign genes, followed by termination codons.

The HIV-1 gp120 coding region was cloned into these two vectors as follows. A synthetic oligonucleotide encoding the 5' end of the gp120 coding sequence following the cleavage site for the HIV-1 signal peptide was generated with the following sequence:

5'-TGACAGAAAAATTGTGGGTCACAGTCTATTTTGGGGTAC
    3' [SEQ ID No. 10]

3'-CATGACTGTCTTTTTAACACCCAGTGT-
    CAGATAAAACCC-5' [SEQ ID No. 11]

This oligonucleotide was cloned into the Kpn I site of pVLBS1egt. The remainder of the gp120 coding sequence was excised as a Kpn 1 fragment from pVLgp120 (Murphy et al., *Gen. Anal. Tech. Appl.* 7:160–171 (1990)) and cloned into the Kpn 1 site of pVLBS 1egt downstream from the synthetic oligonucleotide. The resulting plasmid, pVLBS1egt120, encodes an HIV-1 gp120 protein fused to the signal sequence of egt.

In the second case, a DNA fragment encoding the mature HIV-1 gp120 protein was generated by PCR amplification using pVLgp120 as template and the oligonucleotides 5'-GGCCTGATCACAGAAAAATTGTGGGTC-3' [SEQ ID No. 12] for the 5' end of the gene and 5'-CCCGCCTC-CTCTTCACCACAGTCG-3' [SEQ ID No. 13] for the 3' end. The amplified DNA was cleaved with Bcl I and BamH I and cloned into the BamH I site of pVLBS2p67. The resulting plasmid, pVLBS2p67120 (FIG. 7) [SEQ ID NO: 14,15], encodes an HIV-1 gp120 protein fused to the signal sequence of p67.

Preparation of Cell Extracts and Western Blotting

A 100 ml spinner flask of Sf9 cells was split equally into three spinner flasks each containing 100 ml of medium. When cells reached a density of approximately $1.5 \times 10^6$ cells per ml they were infected with recombinant virus at a multiplicity of infection (MOI) of 1. At the desired times after infection, 1 ml aliquots were removed. The cells were pelleted at 13,000 rpm for 2 minutes and the medium removed for analysis. The cells were washed once with phosphate buffered saline ["PBS": 0.01M $NaPO_4$ (pH 7.4), 0.14M NaCl]. Cell extracts were prepared by resuspending the cells in 0.15 ml NP40 extraction buffer [50 mM Tris HCl (pH8.0), 100 mM NaCl, 1% Nonidet P-40] at 4° C. with rocking. After 10 minutes the extract was spun at 13,000 rpm for 5 minutes to remove the insoluble cellular fraction.

For Western blotting, 1% of the medium fractions and 7.5% of the NP40 soluble (cellular) fractions were analyzed per lane on an SDS-polyacrylamide gel and proteins were transferred to nitrocellulose using a Bio-Rad apparatus. After transfer the nitrocellulose was blocked with TBS [25 mM Tris HCl (pH7.5), 0.5M NaCl] containing 0.1% polyoxyethylene 20 cetyl ether (Brij 58) for 1 hour at room temperature and treated with a polyclonal rabbit anti-HIV-1 envelope antiserum diluted in blocking buffer for 1 hour. The blots were washed three times in TBS and incubated for 1 hour with a 1:2500 dilution of anti-rabbit immunoglobulin G horseradish peroxidase (HRP) conjugate in TBS. After three more washes in TBS, the blots were developed with 4-chloronaphthol (Bio-Rad).

Scale-Up of Protein Production

Two 5 liter airlift fermenters (LH Fermentation) were used to produce egt-modified gp120 in Sf9 cells. More detailed methods on the use of airlift fermenters can be found elsewhere (Murphy, C. I., "Scale-up of protein production in an airlift fermenter in *Baculovirus expression vectors*, (O'Reilly et al., eds.), W.H. Freeman and Co., New York, pp. 249–246 (1992)). Temperature was maintained at 27° C. and dissolved oxygen was kept constant at 50% air saturation. Nitrogen and oxygen were sparged into the vessels at a flow rate of 300 ml per minute. The pH of the medium during cell growth and baculovirus infection consistently remained between 6.0 and 6.5 and was not regulated.

Alternatively, Sf9 cells were grown in a 6 liter Bellco spinner flask fitted with a perfusion wand. The screen tip of the wand was removed to reduce foaming of the medium. Temperature was maintained at 27° C. by wrapping the vessel in a length of ¼ inch I.D. silicone tubing through which warm water was circulated. Air was pumped through the perfusion wand at a flow rate of 500 ml per minute and the wand was driven by an overhead motor operating at 80 rpm.

Fermenter cultures were established with 1 liter seed cultures grown to densities of $1.5–2.5 \times 10^6$ cells per ml in 3 liter Bellco spinner flasks. Enough seed culture cells were used to yield an initial density of $4–5 \times 10^5$ cells per ml in the fermenter. When cell density reached $1.5–2.0 \times 10^6$ cells per ml, high titer ($>1 \times 10^8$ pfu per ml) baculovirus was added. Cells were infected at an MOI between 1 and 5 and harvested after two to three days. Cells were separated from the medium by centrifugation (1500× g) for 20 minutes.

Purification of HIV-1 gp120

HIV-1 gp120 was purified from culture medium by lectin affinity chromatography alone, immunoaffinity chromatography alone, or by sequential application of these two steps. Each preparation was analyzed for total protein and for gp120, qualitatively by Western blot and quantitatively by BCA and antigen capture ELISA. These analyses allowed calculation of the relative purity and recovery of gp120 obtained by each approach. The methods and calculations used are outlined below.

Culture medium from baculovirus-infected insect cell culture was separated from cells by centrifugation, dialyzed for 24 hr at 4 ° C. against TBS [20 mM Tris HCl (pH 7.4), 0.5M NaCl] and centrifuged again. Lentil lectin-Sepharose was added to the medium at a ratio of 10 ml gel to 200 ml medium. The mixture was agitated gently overnight at 4° C. The Sepharose was collected, washed with TBS, 0.5% NP-40 in TBS, and then with TBS again. Bound protein was recovered by slowly eluting with 0.15M methyl alpha D-mannopyranoside in TBS.

Immunoaffinity chromatography was carried out using a monoclonal antibody against HIV-1 gp120 immobilized on N-hydroxysuccinimide-derivatized agarose as follows. Immunoglobulin was isolated from ascites fluid by ammonium sulfate precipitation, then linked to Affi-Gel 10 (Bio-Rad) according to manufacturer's instructions at 5–10 mg per ml gel. The immunoaffinity gel was then added to culture medium or to lentil lectin eluate at a ratio of 25 ml gel to 200 ml medium or 50 ml of lectin-purified material, and agitated overnight at 4° C. The gel was collected and washed with TBS, 1% NP-40 in TBS, and TBS again. Bound protein was recovered by slowly eluting with 3M NaSCN. This material was dialyzed extensively against PBS prior to storage or subsequent use.

Characterization of HIV-1 gp120

The preparations obtained as described above were qualitatively assessed by SDS-PAGE and Western blot analysis. HIV-1 gp120 or fragments of this protein were identified by reaction with serum from rabbits immunized with a recombinant HIV-1 envelope protein purified from *E. coli* (Beltz et al., "Development of assays to detect HIV-1, HIV-2, and HTLV-I antibodies using recombinant antigens", in *Molecular Probes: Technology and Medical Applications*, (Albertini et al., eds.) Reven Press, New York, pp. 131–142 (1987)). Proteins native to the host insect cell or virus were identified by reaction with serum from rabbits immunized with solubilized insect cells infected with wild type baculovirus.

HIV-1 gp120 preparations were quantitatively analyzed for total protein and HIV-1 gp120 content. Total protein was determined by BCA assay (Pierce) using bovine serum albumin (BSA) as a standard. HIV-1 gp120 was quantitated using an antigen-capture ELISA utilizing a goat serum prepared against HIV-1 envelope as the capture antibody, and the same serum conjugated to HRP as the detecting antibody.

Purity and recovery of HIV-1 gp120 in each preparation were calculated by defining the purity of HIV-1 gp120 prepared by sequential lectin and immunoaffinity procedures as 100% and using the BCA results on this material as a standard to quantitatively interpret the ELISA results. The use of this preparation as a standard was based on the absence of insect cell protein in the preparation as determined by Western blot analysis (see Results). The HIV-1 gp120 purity of all the other preparations was calculated by comparing the amount of gp120 in the preparation, determined by ELISA, with the total protein value, determined by BCA. Recovery of HIV-1 gp120 at any step was calculated by dividing the amount of HIV-1 gp120 at that step, determined by ELISA, by the amount of gp120 in the initial medium, also determined by ELISA.

To determine the N-terminal amino acid sequence of secreted gp120, the protein was subjected to SDS-PAGE, electroblotted onto PVDF membrane, stained and excised, and then analyzed using an Applied Biosystems 477A Protein Sequencer.

RESULTS

Construction of *Baculovirus* Secretion Vectors

Two baculovirus expression vectors were designed to incorporate the coding regions for the egt and p67 signal peptides. These coding regions were inserted into pVL941 as synthetic double stranded oligonucleotides (FIG. 6). The DNA sequence of the egt coding region was not known at the time the expression vectors were made so a DNA sequence was deduced from the published egt amino acid sequence (O'Reilly and Miller, *Science* 245:1110–1112 (1989); FIG. 7). Subsequently, it was determined that there are a few differences from the authentic sequence occurring in the third position of some codons (O'Reilly and Miller, *J. Virol.* 64:1321–1328 (1990)). The egt double stranded oligonucleotide was synthesized with a 5' BamH I compatible end and a 3' Kpn I end. The proposed cleavage site for the egt signal peptide was included in the oligonucleotide and was immediately followed by the Kpn I site. This site could then be used for insertion of recombinant genes.

The DNA coding region for the p67 signal peptide was taken from the published sequence (Whitford et al., *J. Virol* 63:1393–1399 (1989); FIG. 7 [SEQ ID NO: 18, 19]). The double stranded oligonucleotide contained a Ban H1 compatible 5' end and a 3' Kpn I end. The two codons on either side of the proposed cleavage site were preserved and a BamH I site was placed after these codons for insertion of foreign genes.

The coding region for the mature gp120 protein (i.e. without the HIV-1 envelope signal peptide) was inserted either as two Kpn I fragments into the egt vector or as a Bcl I/BamH I PCR fragment into the p67 vector (see Materials and Methods). In both cases the reading frame for gp120 was preserved and two extra amino acids were present at the amino terminus due to the restriction endonuclease cleavage sites (FIG. 7).

Comparison of gp120 Expression and Secretion Using Three Signal Peptides

Figure 8A:
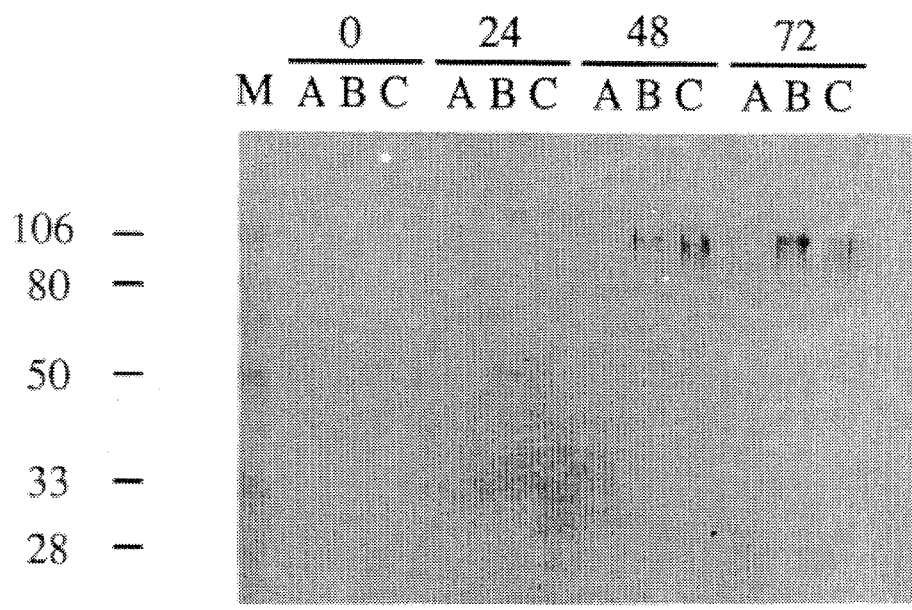
FIGS. 8A and 8B show a comparison by Western blot of gp120 expression using the HIV-1 envelope, egt and p67 signal peptides. Sf9 cells were infected with vHIV120 (A), vegt120 (B), or vp67120 (C) and samples were taken at 0, 24, 48 and 72 hours postinfection and processed as described in Materials and Methods. Samples were analyzed on SDS-polyacrylamide gels and transferred to nitrocellulose for Western blotting. Blots were probed with a rabbit antiserum specific for the HIV-1 envelope protein.
Figure 8B:
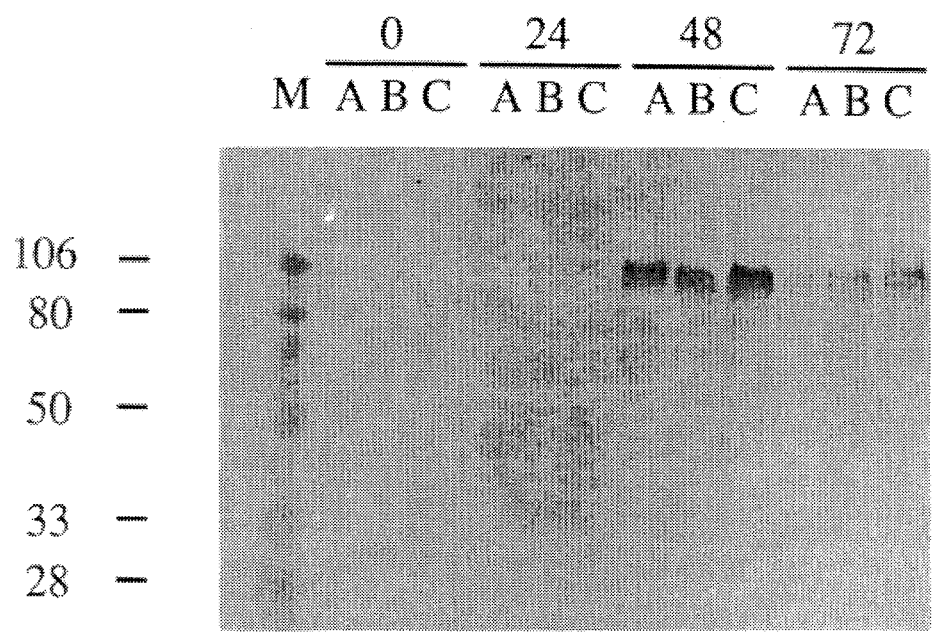
Figure 9:
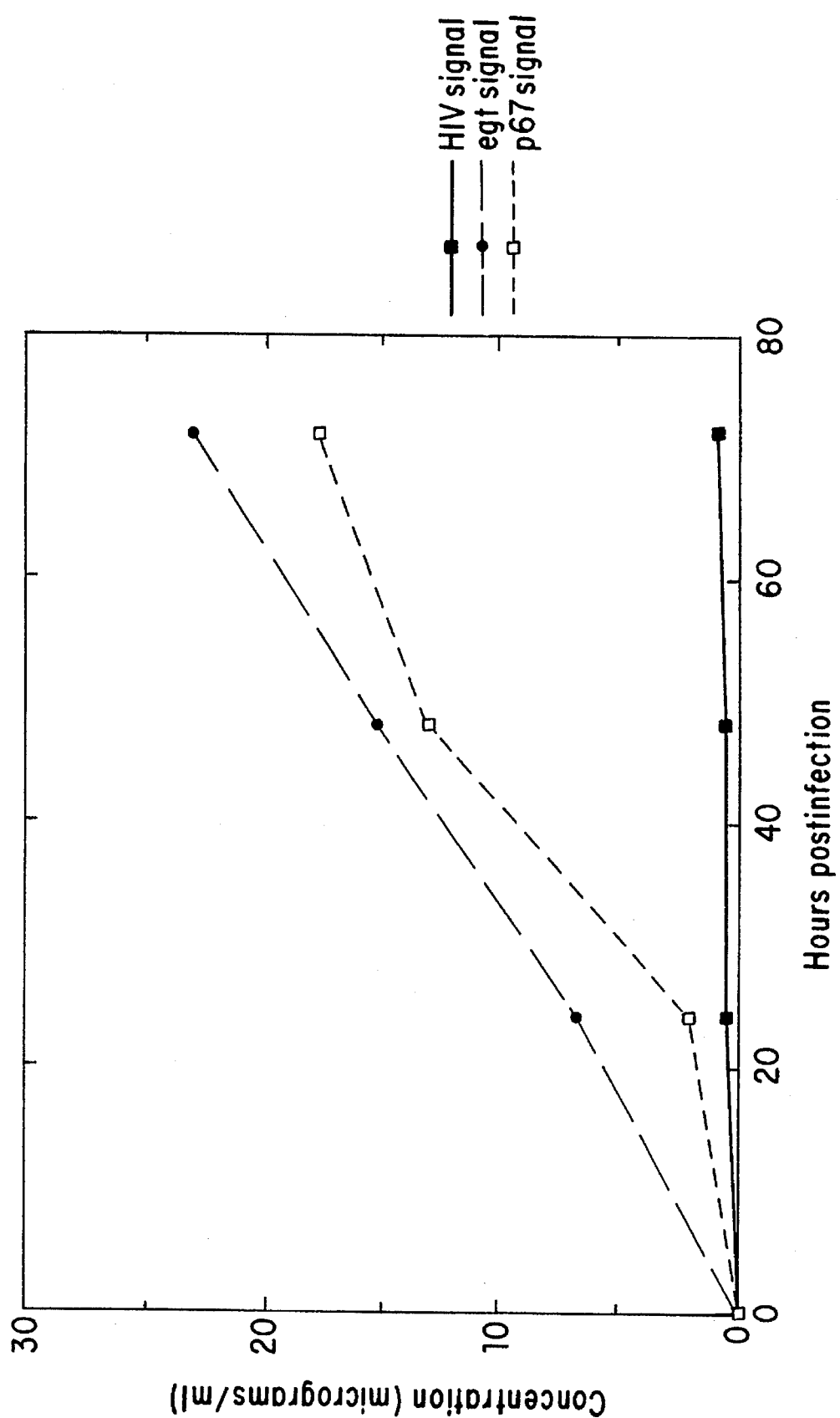
FIG. 9 shows a comparison by ELISA of secreted gp120 concentration using the HIV-1 envelope, egt and p67 signal peptides. Sf9 cells were infected with vHIV120 (■), vegt120 (●), or vp67120 (□) and samples were taken at 0, 24, 48 and 72 hours postinfection and analyzed by ELISA as described in Materials and Methods.

The effect of the three different signal peptides (FIG. 7) on the expression and secretion of HIV-1 gp120 was examined using 100 ml spinner cultures of Sf9 cells infected with one of the three recombinant gp120 baculoviruses. Samples from the culture medium and the NP40-soluble cell extract were taken at 0, 24, 48 and 72 hours postinfection and were analyzed by Western blot and antigen-capture ELISA. Equal volumes of each sample were loaded on the SDS-polyacrylamide gels used for the Western blots. Since the total volume of the culture medium samples was about seven times greater than that of the NP40 cell extract samples, this must be taken into account when comparing the Western blot results (FIGS. 8A and 8B). The ELISA results (FIG. 9) were obtained using equal percentages of total secreted or cell bound material for each assay, and thus the values reflect the relative content of gp120 in those two pools.

The Western blots (FIG. 8) show a clear difference between the HIV-120 (A lanes and the egt- (B lanes) and p67 120 (C lanes) baculoviruses in both the amount of soluble cell bound gp120 and secreted gp120. Replacing the HIV envelope signal peptide with either the egt or p67 signal peptides increased both the expression and secretion of gp120 by several fold. Analysis of the total cell bound gp120 (including any NP40 insoluble protein) gave similar results (data not shown). Thus, the increase in gp120 production using the baculovirus signal peptides was not due just to an increase in gp120 solubility.

To obtain a more quantitative analysis of the differences in gp120 concentration among the three recombinant viruses, an antigen-capture ELISA was performed. The ELISA results (FIG. 9) confirm that the egt and p67 signal peptide-modified gp120 proteins were produced at higher levels than the HIV-1 signal peptide-containing gp120. This difference ranged from about 10 fold in the NP-40 soluble cell fraction (data not shown) to 20–30 fold in the culture medium. Total amounts of gp120 secreted into the culture medium were highest using the egt-gp120 with concentrations ranging from 25 to 30 μg per ml. Secretion of gp120 was also more efficient using the egt and p67 signal peptides. Whereas less than 40% of the total soluble gp120 containing the HIV-1 signal peptide was secreted, over 60% of the total soluble egt- or p67-gp120 was found in the culture medium.

Amino terminal sequencing was performed on both the egt- and p67-120 secreted proteins to determine whether the actual site of signal peptide cleavage was as predicted in FIG. 7. The sequence obtained for egt-120 was ala-val-leu-thr-glu- as predicted, but the sequence for p67-120 was ala-glu-his-cys-asn-gly-ile-thr-glu-, four amino acids prior to the predicted site. Both recombinant proteins were cleaved between the two alanine residues in the signal sequence, even though the native p67 protein is cleaved after the cysteine residue. The reason for the difference in the p67 cleavage site is unknown. It may thus be necessary in future constructions to remove the DNA sequence encoding the amino acids glu-his-cys-asn to avoid additional amino acids on the recombinant protein (see below).

As another way of characterizing the egt- and p67-modified gp120 proteins we tested their ability to bind to soluble CD4, an assay considered to be a measure of gp120 native structure (Kowalski et al., *Science* 247:135 1–1355 (1987)). Using an HIV gp120/CD4 receptor EIA kit (Dupont), it was found that egt-gp120 bound to CD4 as well as unmodified gp120, but only 25% of p67-gp120 bound to CD4 (data not shown). The reasons for this are uncertain but may be the result of the extra seven non-gp120 amino acids at the amino terminus of the mature p67-120 protein.

Comparison of gp120 Function Using Three Signal Peptides

The ability of recombinant gp120 to bind to CD4 was tested using the HIV gp120/CD4 receptor EIA kit from DuPont/NEN. Equal amounts of HIV-120, egt-120, and p67-120 as measured by ELISA using an anti-gp120 antibody were analyzed for CD4 binding. The value obtained for HIV-120 was taken as 100% binding to CD4. The values obtained for egt-120 and p67-120 were 98% and 25%, respectively.

Purification and characterization of gp120

Figure 10B:
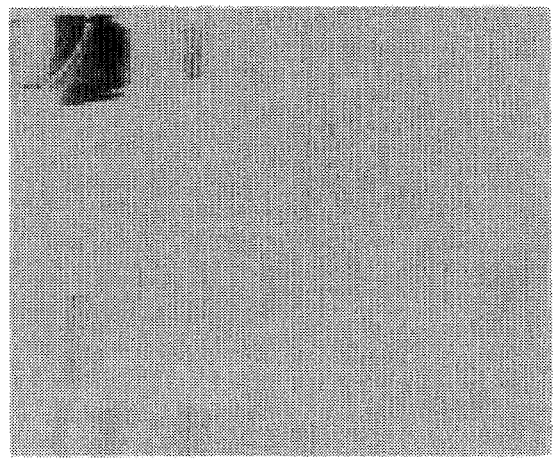
FIGS. 10A and 10B show the immunoaffinity purification of HIV-1 gp120. Medium was prepared from vegt120-infected insect cell culture, and subjected to immunoaffinity purification as described in the text. Samples were analyzed by SDS-PAGE and Coomassie staining (FIG. 10A) or Western blotting (FIG. 10B) against HIV-1 envelope positive rabbit serum. Lane 1: medium from infected cells. Lane 2: Material not bound to antibody linked to Affi-Gel. Lane 3: TBS wash of AffioGel. Lane 4: NaSCN elution of Affi-Gel.
Figure 10A:
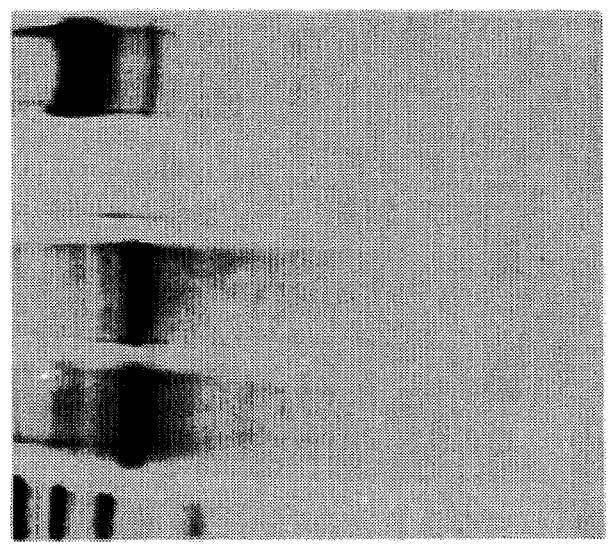

To demonstrate the feasibility of purifying secreted recombinant protein, two steps were applied to the purification of gp120 from the cell culture medium, one specific for HIV-1 gp120, the other likely to be applicable to any secreted glycoprotein. Immunoaffinity purification, using a monoclonal antibody against HIV-1 gp120, was a very effective and efficient purification method (FIG. 10). The eluted protein appeared to be a single diffuse band by SDS-PAGE and Coomassie blue staining or Western blotting against HIV-1 envelope-positive antiserum (FIGS. 10A and 10B). Western blotting using antiserum positive for insect cell proteins detected faint but indistinct reactivity (data not shown). Quantitative analysis of this preparation by BCA and gp120 ELISA indicated that immunoreactive HIV-1 gp120 comprised 98% of the total protein (Table 1). Recovery from the medium was 81% of the starting gp120, or about 15 mg purified protein per liter of medium. Similar results were obtained using lentil lectin-Sepharose chromatography of the medium. However, the eluted material displayed minor but visible insect cell protein bands both by Coomassie staining and Western blotting (data not shown). Quantitative analysis reflected this lower purity of 90%, and also a lower recovery, 69% of starting material (Table 1). The sequential use of these two steps (immunoaffinity followed by lectin chromatography) produced material that revealed no insect cell protein by Coomassie stain or Western blotting (data not shown). This preparation was defined as having 100% immunoreactive purity for purposes of the quantitative analysis. HIV-1 gp120 recovery for the two-step procedure was 50% of the starting material (Table 1).

TABLE 1

| | Purification of HIV-1 gp120 | | | | |
|---|---|---|---|---|---|
| Step | Total protein (mg) | Total gp120 (mg) | gp120 purity (%) | Fold-enrichment | gp120 recovery (%) |
| 1. medium[a] | 444 | 18.8 | 4.2 | — | 100 |
| 2. immuno-affinity | 15.5 | 15.2 | 98 | 23.3 | 81 |
| 1. medium[a] | 444 | 18.8 | 4.2 | — | 100 |
| 2. lentil lectin | 14.4 | 13.0 | 90 | 21.4 | 69 |
| 1. medium[a] | 444 | 18.8 | 4.2 | — | 100 |
| 2. immuno-affinity | 15.5 | 15.2 | 98 | 23.3 | 81 |
| 3. lentil lectin | 9.4 | 9.4 | 100 | 23.8 | 50 |

[a]The results are normalized to 1 liter of starting medium.

DISCUSSION

For many heterologous proteins expressed using the baculovirus system, cloning the gene of interest into one of the widely available standard baculovirus expression vectors results in recombinant protein production levels ranging from 50 to 500 μg per ml (Luckow, V. A., "Cloning and expression of heterologous genes in insect cells with baculovirus vectors," in *Recombinant DNA Technology and Applications*, Prokop et al., eds., McGraw-Hill, New York, pp. 97–152). The results we have presented here show that expression and secretion levels for HIV-1 gp120, a highly glycosylated secreted protein, could be improved up to 20 fold by substituting the HIV-1 envelope signal peptide with signal peptides derived from two baculovirus proteins, egt and p67. One possible reason for the increased expression and secretion of gp120 using these peptides may be that they are derived from AcMNPV proteins and thus are more efficiently recognized by the host cell secretory pathway. However, since individual signal peptides of both eukaryotic and prokaryotic origin show a low degree of sequence conservation and are identified primarily only by a hydrophobic core region (von Heijne, G., *EMBO J.* 3:2315–2318 (1984); von Heijne, G. *J. Mol. Biol.* 184:99–105 (1985)), this explanation may not be sufficient to account for these results.

Several studies have shown that using a heterologous signal peptide fused to a recombinant protein allows efficient secretion of the protein. In mammalian cell expression systems the human interleukin-2 and tissue plasminogen activator signal peptides have been employed to increase secretion of several different proteins (Sasada et al., *Cell Struct. and Func.* 13:129–141 (1988); Champman et al., *Nucl. Acids Res.* 19:3979–3986 (1991); Planelles et al., *AIDS Res. Hum. Reit.* 7:889–898 (1991)). Using the baculovirus expression system, Tessier et al., *Gene* 98:177–183 (1991), fused the papain precursor to signal peptides of insect origin, either from honeybee melittin or *Drosophila melanogaster* α-amylase, and expressed propapain in insect cells. Secretion of propapain was increased 5 fold using the honeybee melittin peptide but the propapain fused to the α-amylase signal peptide was not secreted. Others have shown that the signal peptide from α-galactosidase, a highly secreted yeast protein, when fused to two heterologous proteins, resulted in very little secretion of these proteins from yeast cells (Hofmann and Schultz, *Gene* 101:105–111 (1991)). However, when this signal peptide was modified by mutation, two mutants were found which dramatically increased the secretion of the heterologous proteins. In another experiment a truncated form of a bacterial endoglucanase was secreted efficiently in CHO cells when fused to either a eukaryotic or prokaryotic signal peptide (Hall et al., *J. Biol. Chem.* 265:19996–19999 (1992)). Thus it appears that the signal peptide can have a significant effect on expression and secretion of a given protein but this effect may not necessarily be predictable based on the assumption of better recognition by the host cell.

Conversely, the homologous signal peptide itself does not function well in certain expression systems. This has proven to be the case with the HIV-1 signal peptide in mammalian cells. HIV-1 gp120 and gp160 expression was inefficient in CHO (Laskey et al., *Science* 243:209–212 (1986)) and COS-7 (Champman et al., *Nucl. Acids Res.* 19:3979–3986 (1991)) cells, respectively, but was markedly increased in both cases when a heterologous signal peptide was substituted for the HIV-1 signal peptide. This observation has been attributed to the novel sequence arrangement of the HIV-1 signal peptide (Laskey et al., *Science* 243:209–212 (1986)), which scores poorly in signal prediction programs (Ellerbrok et al., *J. Virol* 66:5114–5118 (1992)). Also, expression of HIV-1 envelope genes containing the homologous signal sequence may be rev-dependent (Champman et al., *Nucl. Acids Res.* 19:3979–3986 (1991)). In insect cells there may be some toxicity associated with the HIV-1 signal peptide since there is a much faster decrease in cell viability upon infection with virus containing this peptide (Murphy, unpublished observations). Thus, there may be several explanations for the increased expression of HIV-1 gp120 using the egt and p67 signal peptides. However, the poor expression associated with the HIV-1 signal peptide is not a major factor in this increase because the egt and p67 signal peptides are effective in increasing expression and secretion of other envelope proteins, such as feline immunodeficiency virus (FIV) and HIV-2 (Murphy et al., unpublished observations).

In summary, the baculovirus derived signal peptides egt and p67 were very useful in generating large amounts of secreted HIV-1 gp120 from infected insect cells. The secreted gp120 could be readily isolated from the culture medium of baculovirus-infected cells in just one or two purification steps. The purification requirements were simplified by the relatively high purity of HIV-1 gp120 in the starting medium: since the culture medium is serum-free, the conditioned medium was composed primarily of HIV-1 gp120. We have routinely been able to purify 10 to 15 mg per liter of gp120 from infected insect cells, a number 10 fold above that for gp120 produced in *Drosophila* cells (Culp et al., *Biotechnology* 9:173–177 (1991)) and gp120 containing the HIV-1 signal peptide produced in Sf9 cells. The yield of gp120 reported here make this system very useful for producing the quantities of protein necessary for vaccine development and protein and carbohydrate analysis.

The vectors described here have been used to generate recombinant virus which can then be used for protein expression in Sf9 cells in a batch type system. These signal peptide coding regions could also be used in vectors to generate a continuous insect cell line which produces a recombinant protein constitutively. For example, a vector used to transform insect cells has been described by Jarvis et al., *Biotechnology* 8:950–955 (1990). The vector contained an early *Baculovirus* promoter from the IE1 gene to produce an Sf9 cell line which expressed human TPA. A vector such as this may be modified by the insertion of a signal peptide coding region upstream of, and in frame with, the recombinant protein coding region. The polyhedrin promoter cannot be used in this system because it is regulated by other *Baculovirus* proteins.

Although for purposes of clarity and understanding the foregoing invention has been described in some detail by way of illustration and example, it will be obvious that certain changes and modifications may be practiced within the scope of the following claims.

What is claimed is:

1. A vector for expression and secretion of foreign proteins in insect host cells comprising a *Baculovirus* promoter operably linked to an insect virus signal peptide coding region from a baculovirus protein, wherein said signal peptide is derived from a 60 kD protein encoded by the AcMNPV egt gene of *Baculovirus*.

2. A vector for expression and secretion of foreign proteins in insect host cells comprising a *Baculovirus* promoter operably linked to an insect virus signal peptide coding region from a baculovirus protein, wherein said signal peptide is derived from the Baculovirus glycoprotein p67.

3. A host cell transformed with the vector of claims 1 or 2.

4. A recombinant virus generated with the vector of claims 1 or 2.

5. A host cell infected with the virus of claim 4.

6. A method for expressing a glycosylated protein in the late term of a *Baculovirus* infection comprising:
  (a) operably linking a nucleotide sequence encoding said glycosylated protein into the vector of claims 1 or 2 downstream from said signal peptide, said signal peptide selected from the group consisting of peptides encoded by the AcMNPV egt gene, the AcMNPV glycoprotein gene p67 and a *Baculovirus* glycoprotein p67 gene;
  (b) generating a recombinant virus with the operably linked DNA of step (a);
  (c) infecting a host cell with the recombinant virus of step (b) such that said nucleotide sequence is expressed; and
  (d) recovering and purifying the protein.

7. The method of claim 6, said method comprising:
  (a) operably linking a nucleotide sequence encoding a glycosylated protein into the vector of claims 1 or 2 downstream from the nucleotide sequence encoding the signal peptide of the AcMNPV egt gene;
  (b) generating a recombinant virus with the operably linked DNA of step (a);
  (c) infecting a host cell with the recombinant virus of (b) such that said nucleotide sequence is expressed; and
  (d) recovering and purifying the protein.

8. The method of claim 6, said method comprising:
  (a) operably linking a nucleotide sequence encoding a glycosylated protein into the vector of claims 1 or 2 downstream from the nucleotide sequence encoding the signal peptide of the AcMNPV glycoprotein gene p67;
  (b) generating a recombinant virus with the operably linked DNA of step (a);
  (c) infecting a host cell with the recombinant virus of (b) such that said nucleotide sequence is expressed; and
  (d) recovering and purifying the protein.

9. The method of claim 6, said method comprising:
  (a) operably linking a nucleotide sequence encoding a glycosylated protein into the vector of claims 1 or 2 downstream from a nucleotide sequence encoding the signal peptide from a *Baculovirus* glycoprotein p67 gene;
  (b) generating a recombinant virus with the operably linked DNA of step (a);
  (c) infecting a host cell with the recombinant virus of (b) such that said nucleotide sequence is expressed; and
  (d) recovering and purifying the protein.

10. A method for expressing a peptide comprising:
  (a) operably linking a nucleotide sequence encoding said peptide into the vector of claims 1 or 2 downstream from the signal peptide;
  (b) generating a recombinant virus with the operably linked DNA of step (a);
  (c) infecting a host cell with the recombinant virus of step (b) such that said nucleotide sequence is expressed; and
  recovering the peptide.

11. The method of claim 10, wherein said host cell is *Spodoptera frugiperda*.

12. A method for expressing HIV-1 gp120 comprising:
  (a) operably linking a nucleotide sequence encoding a peptide fragment comprising about 450–500 carboxyl terminal amino acids of HIV-1 gp120 downstream from the signal peptide found in the *Baculovirus* vector of claims 1 or 2;

(b) generating a recombinant virus with the operably linked DNA of step (a);

(c) infecting a host cell with the recombinant virus of step (b) such that said nucleotide sequence is expressed; and (d) recovering the peptide.

13. A method for expressing an FIV glycoprotein comprising:

(a) operably linking a nucleotide sequence encoding FIV glycoprotein downstream from the signal peptide found in the *Baculovirus* vector of claims 1 or 2;

(b) generating a recombinant virus with the operably linked DNA of step (a);

(c) infecting a host cell with the recombinant virus of step (b) such that said nucleotide sequence is expressed; and (d) recovering the FIV glycoprotein.

14. A method for expressing a glycosylated protein comprising:

(a) operably linking a nucleotide sequence encoding said glycosylated protein downstream from the signal peptide found in the operably linked DNA vector of claims 1 or 2;

(b) generating a recombinant virus with the operably linked DNA of step (a);

(c) infecting a host cell with the recombinant virus of step (b) such that said nucleotide sequence is expressed; and (d) recovering the protein.

15. A method for expressing a mammalian retrovirus protein comprising:

(a) operably linking a nucleotide sequence encoding said protein downstream from the signal peptide found in the operably linked DNA vector of claims 1 or 2;

(b) generating a recombinant virus with the operably linked DNA of step (a);

(c) infecting a host cell with the recombinant virus of step (b) such that said nucleotide sequence is expressed; and (d) recovering the protein.

16. A method for expressing a glycosylated protein in the late term of a *Baculovirus* infection comprising:

(a) operably linking a nucleotide sequence encoding said glycosylated protein into the vector of claims 1 or 2 downstream from said signal peptide;

(b) generating a recombinant virus with the operably linked DNA of step (a);

(c) infecting a host cell with the recombinant virus of step (b) such that said nucleotide sequence is expressed; and (d) recovering and purifying the protein.

17. The method of claim 16, wherein said promoter is a polyhedrin promoter.

18. A virus comprising the DNA sequence encoding a fusion protein, said fusion protein further comprising a signal peptide derived from a 60 kD protein encoded by the AcMNPV egt gene of *Baculovirus* or a signal peptide derived from the *Baculovirus* p67 gene.

* * * * *

UNITED STATES PATENT AND TRADEMARK OFFICE
CERTIFICATE OF CORRECTION

PATENT NO. : 5,516,657

DATED : May 14, 1996

INVENTORS : Murphy *et al.*

It is certified that an error appears in the above-identified patent and that said Letters Patent is hereby corrected as shown below.

In column 4, at line 19, delete "AffioGel" and insert therein --Affi-Gel--; and at line 33, delete "transcription" and insert therein --translocation--.

In column 8, at line 9, delete "dam" and insert therein --data--.

In column 12, at line 41, delete "Ban H1" and insert therein --BamH I--.

In column 13, at line 8, delete "lanes and" and insert therein --lanes) and--.

Signed and Sealed this

Eleventh Day of February, 1997

*Attest:*

BRUCE LEHMAN

*Attesting Officer*  *Commissioner of Patents and Trademarks*